United States Patent
Hagau et al.

(10) Patent No.: US 8,496,598 B2
(45) Date of Patent: Jul. 30, 2013

(54) APPARATUS FOR EARLY DIAGNOSIS OF CARPAL TUNNEL SYNDROME AND METHOD AND DEVICE FOR ACQUIRING INFORMATION ON THE SKIN SENSITIVITY OF A FINGER OF A PATIENT

(75) Inventors: Serban Hagau, Paris (FR); Jean Alexandre Marie Barge, Besancon (FR)

(73) Assignee: Technologia, Paris (FR)

( * ) Notice: Subject to any disclaimer, the term of this patent is extended or adjusted under 35 U.S.C. 154(b) by 350 days.

(21) Appl. No.: 12/735,622

(22) PCT Filed: Feb. 2, 2009

(86) PCT No.: PCT/FR2009/050151
§ 371 (c)(1),
(2), (4) Date: Sep. 24, 2010

(87) PCT Pub. No.: WO2009/101313
PCT Pub. Date: Aug. 20, 2009

(65) Prior Publication Data
US 2011/0009769 A1     Jan. 13, 2011

(30) Foreign Application Priority Data

Feb. 5, 2008    (FR) ...................................... 08 50716

(51) Int. Cl.
*A61B 19/00*     (2006.01)

(52) U.S. Cl.
USPC .......................................... 600/557; 600/553

(58) Field of Classification Search
USPC ................................................. 600/553, 557
See application file for complete search history.

(56) References Cited

U.S. PATENT DOCUMENTS

| | | | |
|---|---|---|---|
| 3,933,148 A | 1/1976 | Wyler et al. | |
| 4,250,891 A | 2/1981 | Carlson et al. | |
| 4,467,815 A * | 8/1984 | O'Brien et al. | 600/553 |
| 5,381,806 A | 1/1995 | Weinstein et al. | |
| 5,719,561 A * | 2/1998 | Gonzales | 340/7.51 |
| 5,827,828 A | 10/1998 | Buschard et al. | |
| 2010/0331723 A1 * | 12/2010 | Chandrasekar et al. | 600/557 |

FOREIGN PATENT DOCUMENTS

| | | |
|---|---|---|
| EP | 0364158 | * 10/1989 |
| EP | 0 364 158 | 4/1990 |
| EP | 1 792 567 | 6/2007 |
| FR | 2 894 125 | 6/2007 |
| WO | WO 00/59377 | 10/2000 |

OTHER PUBLICATIONS

Rubley et al. "Cryotherapy, Sensation, and Isometric-Force Variability" Journal of Athletic Training 2003, p. 113-118.*

* cited by examiner

*Primary Examiner* — Max Hindenburg
*Assistant Examiner* — Renee Danega
(74) *Attorney, Agent, or Firm* — Jacobson Holman, PLLC

(57) ABSTRACT

The apparatus (2) for early diagnosis of carpal tunnel syndrome, of the type comprising:
receiving means which define a receiving zone (8) for receiving a patient's finger,
means for measuring the cutaneous sensibility of a finger (10) disposed in said receiving means, comprising a device for determining a sensation threshold of the finger pulp and a device for measuring the innervation density of the finger pulp, each device comprising protruding portions (22) adapted to be brought into contact with the finger (10),
is characterized in that the protruding portions (22) of the device for measuring the innervation density are identical with those of the device for determining the sensation threshold.

18 Claims, 3 Drawing Sheets

APPARATUS FOR EARLY DIAGNOSIS OF CARPAL TUNNEL SYNDROME AND METHOD AND DEVICE FOR ACQUIRING INFORMATION ON THE SKIN SENSITIVITY OF A FINGER OF A PATIENT

This is a national stage of PCT/FR09/050151 filed Feb. 2, 2009 and published in French, which has a priority of French no. 0850716 filed Feb. 5, 2008, hereby incorporated by reference.

The present invention relates to an apparatus for the early diagnosis of carpal tunnel syndrome, of the type comprising:
receiving means which define a receiving zone for receiving a patient's finger,
means for measuring the cutaneous sensibility of a finger disposed in said receiving means, comprising a device for determining a sensation threshold of the finger pulp and a device for measuring the innervation density of the finger pulp, each device comprising protruding portions adapted to be brought into contact with the finger.

The present invention relates also to a device and a method for acquiring information relating to the cutaneous sensibility of the patient's finger.

Carpal tunnel syndrome is one of the main musculoskeletal disorders (MSDs) and manifests itself as numbness or pain in some fingers of the hand following compression of nerve and musculotendinous structures in the carpal tunnel. Carpal tunnel syndrome is recognized and indemnified as a professional disease and is becoming considerably more common in the industrialized world.

Even before symptoms of the disease appear, carpal tunnel syndrome can be detected preventively by identifying a loss of sensibility of the pulp of the middle or index finger of the affected hand. According to the teaching of the occupational medicine of Quebec, there are two categories of test for evaluating the cutaneous sensibility of a finger:
innervation density tests, also called discrimination capacity tests, such as, for example, the static two-point discrimination test using a Weber's compass or a Weinstein esthesiometer, or the pinprick test, and
tests of perception of the sensation threshold, such as, for example, the Semmes-Weinstein monofilament test, or tests which evaluate the vibratory threshold.

Apparatuses for diagnosing carpal tunnel syndrome frequently comprise means for measuring the cutaneous sensibility of a finger using one or other of the two categories of test mentioned above.

Document U.S. Pat. No. 5,827,828 describes a device for measuring the innervation density of the finger pulp by means of the "static" two-point discrimination test. The device comprises two rods of identical diameters having rounded ends, the spacing of which is variable. The apparatus measures the force exerted on the finger pulp by the rods that permits perception of the touch by the patient. The rods are gradually moved apart and the device measures the spacing at which the patient perceives the touch of two different rods.

Document EP 0 364 158 A1 describes a device and a method for determining a sensation threshold of the finger pulp. The device comprises a disk and rods distributed axially around the disk, the diameter of which rods varies from 1 mm to 9 mm. The operator manually places the rods in contact with the patient's finger, gradually or randomly increasing the diameter of the rods. The sensation threshold of the finger pulp is a function of the diameter of the first rod perceived by the patient.

Document WO 00/59377 describes an apparatus comprising a device for determining a sensation threshold of the finger pulp by means of tests which evaluate the vibratory threshold. The device comprises a rod of fixed diameter and means for displacing the rod in contact with the finger pulp. During the test, the displacement means cause the rod to vibrate at a predetermined frequency, of from 20 Hz to 50 Hz, preferably 40 Hz, while gradually increasing the amplitude of the vibrations. The sensation threshold is determined as a function of the amplitude at which the patient perceives the vibration of the rod.

However, the diagnosis provided by the apparatuses described in the above-mentioned documents is not complete, because these apparatuses are capable of determining either the innervation density or the sensation threshold of the finger, but not both at the same time.

More rarely, apparatuses for diagnosing carpal tunnel syndrome comprise means for measuring the cutaneous sensibility of a finger by carrying out the two categories of test mentioned above in succession.

Document U.S. Pat. No. 4,250,891 describes an apparatus comprising a device for determining a sensation threshold of the finger pulp and a device for measuring the innervation density of the finger pulp by means of the static two-point discrimination test. The document proposes several embodiments. According to one embodiment, the device for determining the sensation threshold comprises a longitudinally protruding portion having a triangular cross-section which increases gradually in the longitudinal direction. An operator moves the protruding portion in the longitudinal direction in contact with the finger pulp of the patient, who must indicate when he perceives the touch of the protruding portion. The device for measuring the innervation density of the finger pulp comprises two protruding portions of triangular cross-section, the spacing of which gradually varies. During the test, the operator moves the two protruding portions in contact with the finger of the patient, who must indicate when he distinctly perceives both protruding portions.

However, the apparatus described in document U.S. Pat. No. 4,250,891 is entirely manual and gives results that are not very precise and are dependent on the operator who conducts the test.

Document FR 2 894 125 describes an apparatus for diagnosing carpal tunnel syndrome which uses the two categories of test mentioned above and constitutes the closest prior art to the invention. The apparatus comprises a first device for measuring sensibility by cutaneous pressure and a second device for measuring sensibility by cutaneous discrimination, each sensibility-measuring device being associated with a specific receiving zone. The housing of the apparatus accordingly comprises two openings which are in communication with the receiving zones. The first device for measuring by cutaneous pressure comprises a conically shaped element which is to be in contact with the finger with gradually increasing pressure. The measured sensibility is a function of the pressure exerted by the element on the finger. The second measuring device comprises a rotating member provided with a plurality of notches of different sizes on its peripheral surface. The measured sensibility is a function of the width of the smallest notch detected by the patient.

According to another form of the second device, identical protuberances are distributed in pairs and with variable spacing on the peripheral surface of the rotating member. The measured sensibility is a function of the smallest spacing between two protuberances detected by the patient.

However, the device described in document FR 2 894 125 comprises two completely separate devices for the sensation threshold perception test and for the innervation density test, with the risk that there may be considerable dispersion in the results obtained. The sensation threshold determined by cutaneous pressure by means of the first device is not taken into account by the second device, in which the pressure exerted by the rotating member on the finger pulp is not controlled. Furthermore, the housing of the apparatus comprises two openings, which requires that the patient's finger be moved between the two tests and reduces the accuracy of the results obtained. The results obtained with this apparatus are substantially identical to those obtained with two different apparatuses for diagnosing carpal tunnel syndrome, one comprising the first device and the other the second device.

It is an object of the present invention to obtain a more precise evaluation of tactile sensibility by determining in the first instance the sensibility to touch-pressure and in the second instance the discrimination capacity, with the same force as identified in the first instance being applied and without any movement of the patient's finger.

More particularly, it is an object of the invention to reduce the dispersion of the measurements carried out between the sensation threshold perception tests and the innervation density tests and accordingly increase the accuracy of the results obtained, in order to diagnose carpal tunnel syndrome earlier.

To that end, the invention relates to an apparatus for the early diagnosis of carpal tunnel syndrome of the type mentioned above, characterized in that the protruding portions of the device for measuring the innervation density are identical with those of the device for determining the sensation threshold.

According to other embodiments, the apparatus for the early diagnosis of carpal tunnel syndrome has one or more of the following features, taken in isolation or in any technically possible combinations:
  the device for determining the sensation threshold comprises a first set of at least two filaments of different diameters, means for selecting a filament of said first set, and means for displacing the selected filament towards the receiving zone, parallel to the direction of said selected filament,
  the device for measuring the innervation density of the finger comprises a pair of identical sets of filaments, each set comprising at least two filaments of different diameters, means for selecting a pair of filaments of identical diameters and positioning them parallel with one another, each filament of said pair belonging to one of said sets of filaments, means for adjusting the distance between the filaments of the selected pair, and means for displacing the selected pair of filaments towards the receiving zone parallel to the direction of said filaments of the selected pair,
  the set of filaments of the device for determining the sensation threshold is one of the two sets of filaments of the device for measuring the innervation density,
  the apparatus comprises a shaft and at least one support means, which is mounted freely in rotation about the shaft and is displaceable in translation in a direction perpendicular to the shaft, each set of filaments being disposed on a support means, said filaments being oriented in radial directions relative to the shaft,
  the displacement means comprise a slide for supporting the shaft, means for supporting said slide in translation, and a first cam which is arranged to displace the slide along the support means in an alternating movement in the direction towards, and then away from, the receiving zone,
  the selection means, or the selection and positioning means, respectively, comprise a second cam which is arranged to cause each support means to rotate about the shaft,
  the apparatus comprises means for disengaging the selection means, respectively for selecting and positioning means, so as to allow an operator conducting a test for measuring the sensibility of the patient's finger to orient a chosen filament, respectively a chosen pair of filaments, towards the receiving zone,
  the adjustment means comprise a ratchet wheel mounted for rotation on the shaft, said wheel being in contact with a spring leaf, a first support means being integral in translation with the ratchet wheel and a second support means being free in translation relative to said wheel in its axial direction, an internally threaded element mounted on the second support means, a rod which is integral with the ratchet wheel at one end, is threaded at the other end, and is mounted inside the shaft, and means for translation of the internally threaded element towards a position in which it is engaged on the threaded rod, so that, when the internally threaded element is in the engaged position on the threaded rod, each translation of the slide away from the receiving zone causes rotation of the ratchet wheel, causing translation of the second support means relative to the first support means in the axial direction of the shaft, said translation altering the distance between the filaments of the selected pair,
  the apparatus comprises an electrical device for driving each cam in rotation,
  the apparatus comprises means for determining the selected filament, respectively the selected pair of filaments,
  the apparatus comprises means for determining the distance between the filaments of the selected pair.

The invention relates also to an acquisition device of the type mentioned above, characterized in that it comprises an apparatus for the early diagnosis of carpal tunnel syndrome as defined above, and means for storing the output signals of the determination means.

The invention relates also to a method of acquiring information relating to the cutaneous sensibility of a finger of a patient by means of a device for acquiring said information, said device comprising a pair of identical sets of filaments, and said method comprising steps in which:
  a sensation threshold of the finger pulp is measured and stored by determining the minimum diameter of the filament of a first set of filaments for which the patient perceives the touch of said filament, and
  without the patient's finger moving in relation to the preceding step, an innervation density of the finger pulp is measured and stored by determining the minimum spacing between two filaments, which are identical and have the diameter determined in the preceding step, for which the patient distinctly perceives the touch of both filaments.

According to other embodiments, the method of acquiring information comprises one or more of the following features, taken in isolation or in any technically possible combinations:
  the method comprises, for measuring and storing the sensation threshold of the finger pulp, steps in which:
  filaments of the first set are brought into contact, in succession, with the finger pulp, according to an increasing or random progression of their diameters,
  the number of the filament for which the patient perceives the touch of said filament is determined, and
  the number of said filament is stored;

the method comprises, for measuring and storing the innervation density of the finger pulp, steps in which:

a pair of filaments having the diameter determined in the step of measuring the sensation threshold of the finger pulp is brought into contact with the finger pulp, with an initial spacing of about 1 mm, the two filaments of said pair of filaments are gradually moved apart, the minimum distance between said two filaments for which the patient distinctly perceives the touch of both filaments is determined, and said minimum distance is stored.

The invention and its advantages will be better understood upon reading the following description, which is given solely by way of example and with reference to the accompanying drawings, in which.

In the following description, the terms "front", "back", "top", "bottom", "longitudinal", "transverse" and "vertical" are to be interpreted by reference to the orthogonal axis system shown in the figures and having:

a longitudinal axis X directed from the back to the front,
a transverse axis Y directed from the right to the left, and
a vertical axis Z directed from the bottom to the top.

Figure 1:
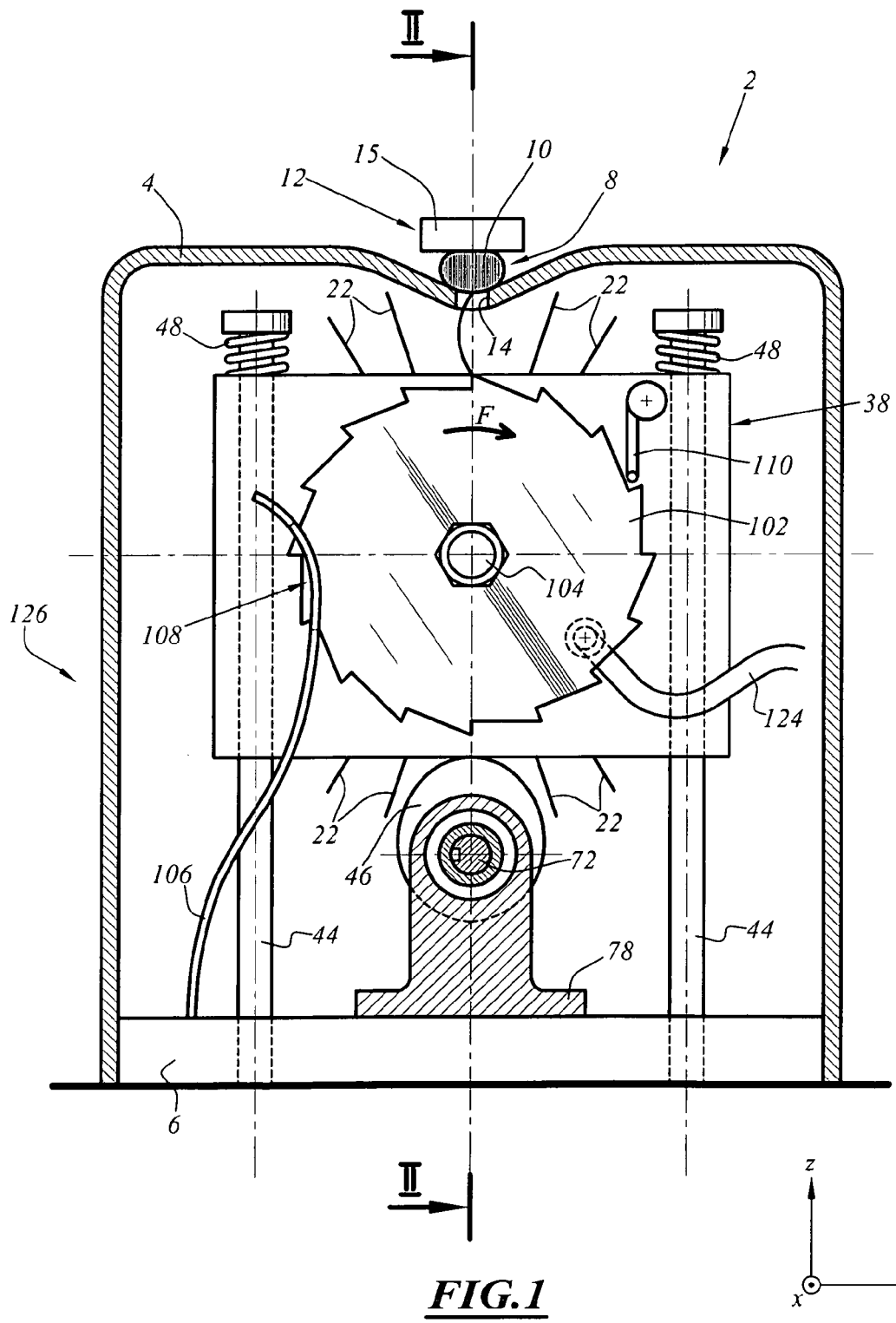
FIG. 1 is a front view, in transverse section along line I-I of FIG. 2, of an apparatus for the early diagnosis of carpal tunnel syndrome according to the invention.

In FIG. 1, an apparatus 2 for the early diagnosis of carpal tunnel syndrome comprises a cap 4 fixed to a base 6. The apparatus 2 comprises a receiving zone 8 for the patient's finger 10, and positioning means 12 for the finger 10. The cap 4 has a single opening 14 which is in communication with the receiving zone 8.

The positioning means 12 comprise a felt pad 15 for holding the finger 10 on the cap 4, and a stop (not shown) for the longitudinal positioning of the finger in the zone 8.

Figure 2:
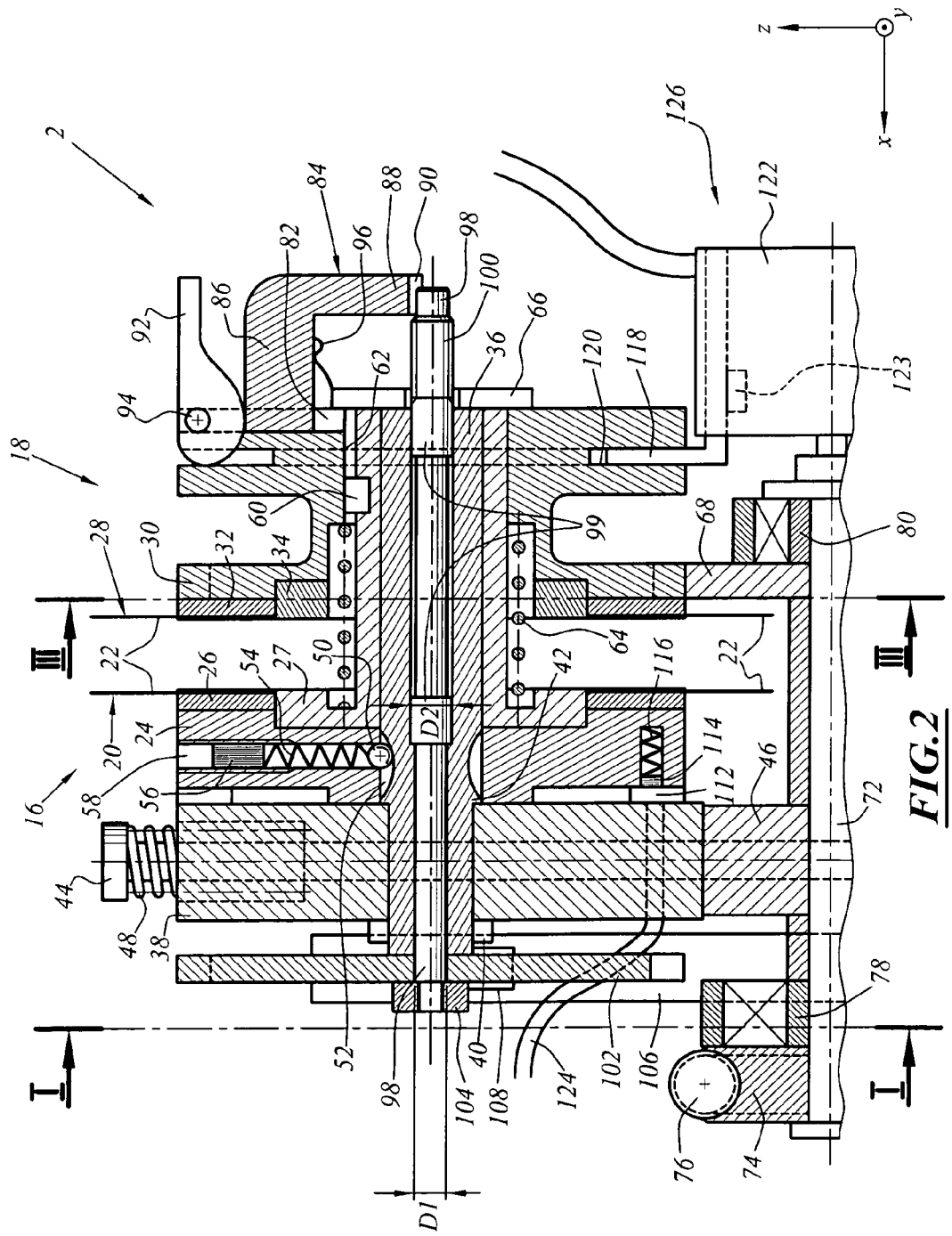
FIG. 2 is a partial side view, in longitudinal section along line II-II of FIG. 1, of the apparatus according to the invention.

In FIG. 2, the apparatus for early diagnosis 2 comprises a first device 16 for determining a sensation threshold of the finger pulp and a second device 18 for measuring the innervation density of the finger pulp.

The first device 16 comprises a first set 20 of filaments 22 of different diameters, which filaments 22 are fixed to a first circular plate 24 by way of a collar 26. The filaments 22 are disposed in different radial directions and are equally distributed in terms of angle. The filaments 22 are disposed in order of increasing diameter.

The collar 26 is an overmoulding produced from a resilient product, for example of the silicone or polyurethane type. The collar 26 is fastened on the plate 24 by a ring 27, which is itself fixed to the plate 24 by screws (not shown).

The second device 18 comprises the above-mentioned elements of the first device 16 as well as a second set 28 of filaments 22 of different diameters which are fixed to a second circular plate 30 by way of a collar 32. The circular plate 32 has an H-shaped longitudinal cross-section and comprises a front face and a back face, the front face being in contact with the collar 32.

The filaments 22 of the second set 28 are disposed radially relative to the plate 30 and are equally distributed in terms of angle.

The collar 32 is an overmoulding produced from a resilient product, for example of the silicone or polyurethane type. The collar 32 is fastened on the plate 30 by a ring 34, which is itself fixed to the plate 30 by screws (not shown).

The filaments 22 of the second set 28 are held on the second plate 30 by the collar 32 and the ring 34 so that the filaments of the same diameter of the sets 20, 28 are facing.

The two plates 24, 30 are mounted to be freely rotatable on a hollow shaft 36.

The hollow shaft 36 passes through a slide 38. The shaft 36 is integral in translation and in rotation with said slide 38 by way of a nut 40 and a hard shank 42. The slide 38 is guided by two columns 44, which are themselves fixed to the base 6. The slide 38 is held in abutment on a first cam 46 by springs 48.

The cam 46 is arranged to displace the slide 38 vertically between a bottom position and a top position. FIG. 1 corresponds to a top position of the slide 38, and FIG. 2 corresponds to a bottom position of the slide 38.

The first plate 24 is positioned on the hollow shaft 36 by way of a ball 50 which engages in grooves 52 cut into the hollow shaft 36 on its periphery. A spring 54 holds the ball 50 in contact with the shaft 36. The number of grooves 52 in the hollow shaft 36 is equal to the number of filaments 22 of the first set 20. The force exerted by the spring 54 can be adjusted with the aid of an element 56 which is screwed into an internal thread 58, the element 56 thus compressing the spring 54 on the ball 50.

The ring 27 for fastening the first plate 24 carries a pin 60 which slides in a groove 62 of the second plate 30. The two plates 24 and 30 are thus integral in rotation by way of the pin 60 and the groove 62. A spring 64, in abutment on the ring 27 and on the second plate 30, is arranged to hold the second plate 30 longitudinally away from the first plate 24. The two plates 24, 30 are free in translation relative to one another. The totality of the two plates 24, 30 is held in translation on the hollow shaft 36, on one side by the slide 38 and on the other side by a circular stop 66. The maximum longitudinal spacing between the two plates 24, 30 is, for example, 25 mm.

Figure 3:
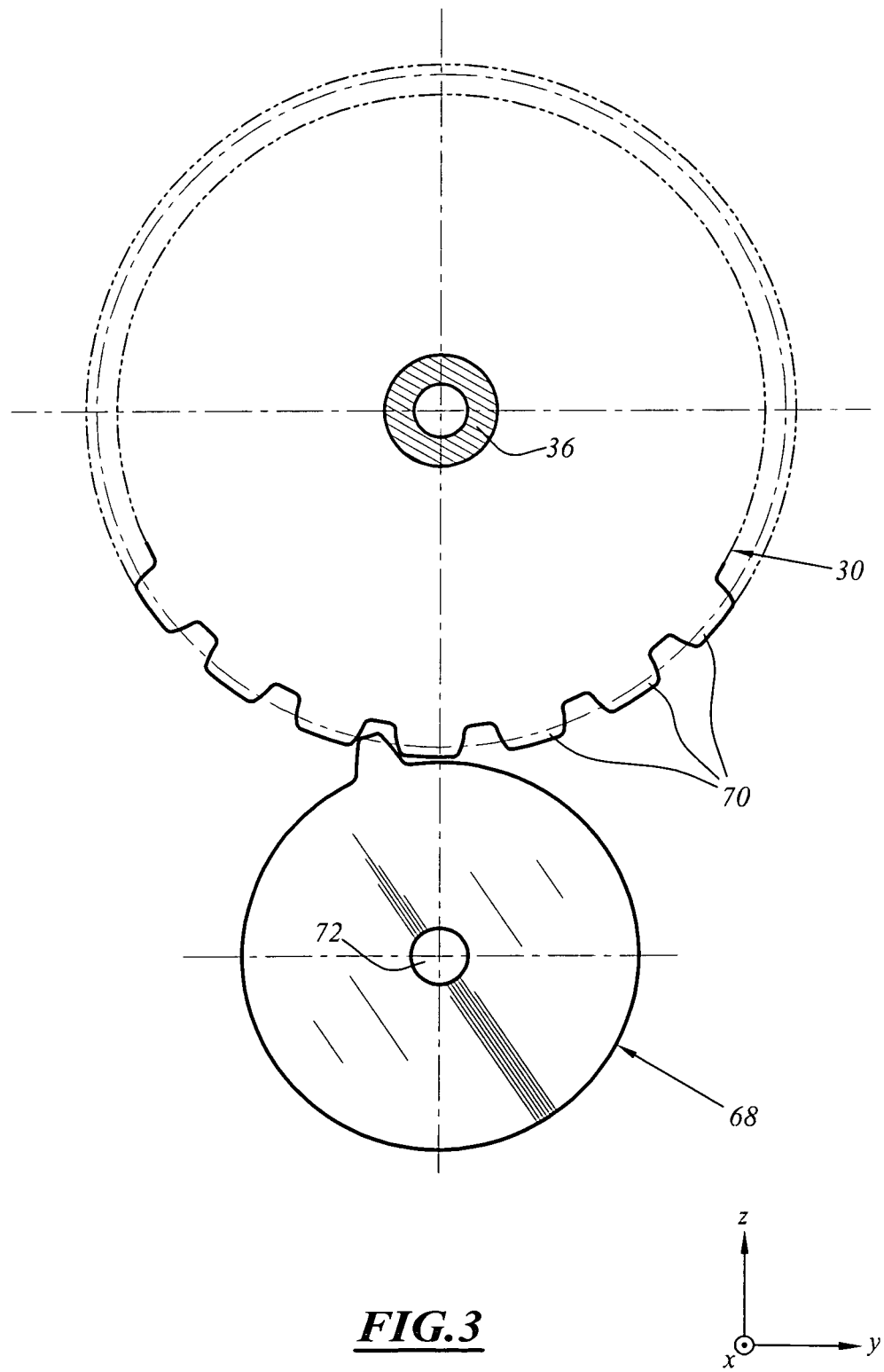
FIG. 3 is a simplified partial view, in transverse section along line III-III of FIG. 2, of the apparatus according to the invention.

A second cam 68 having a single tooth is arranged to drive in rotation the second plate 30, which is provided with teeth 70 on its periphery. The number of teeth 70 is equal to the number of filaments 22 of the first set 20. The system for driving the plate 30 in rotation by way of the cam 68 is shown in a simplified view in FIG. 3, in which, in particular, the rings 27, 34 and the spring 64 are not shown.

The cams 46, 68 are integral by wedging with a rotary shaft 72. The two cams 46, 68 are positioned angularly so as to drive the plate 30 in rotation only when the slide 38 is in the bottom position.

A wheel 74, having an internal thread at its periphery, is integral with the shaft 72 by wedging. An endless screw 76 in contact with the internal thread of the wheel 74 is arranged to drive said wheel 74 in rotation. The endless screw 76 is itself driven in rotation about a transverse axis by the single motor (not shown) of the apparatus 2. The motor is electric and operates at continuous low voltage. The shaft 72, the wheel 74 and the screw 76 are carried by bearings 78, 80 fixed to the base 6.

A dovetail groove 82 is formed on the back face of the plate 30, radially relative to the hollow shaft 36.

An element 84, of bent shape, is arranged to slide in the groove 82. The element 84 comprises a first, substantially horizontal portion 86, the end of which is in contact with the groove 82, and a second, substantially vertical portion 88, the end of which is provided with an internal thread 90.

A cam 92, articulated about a shaft 94 integral with the plate 30, is in abutment on the top face of the first portion 86, and a return spring 96 is in abutment on the bottom face of the first portion 86. The cam 92 is capable of rotating through about 90° between a substantially vertical position and a substantially horizontal position.

The cam 92 is arranged to cause the element 84 to slide vertically between a top position and a bottom position. The substantially vertical position of the cam 92 corresponds to the top position of the element 84. The substantially horizontal position of the cam 92 corresponds to the bottom position of the element 84, as shown in FIG. 2.

A rod 98 is mounted freely in rotation inside the hollow shaft 36. The rod 98 protrudes from the hollow shaft 36 on each side and is provided at its back end with a thread 100. A ratchet wheel 102 is mounted integrally about the front end of the rod 98.

The inner cavity of the hollow shaft 36 has a first diameter D1 over a front portion of its length and a second diameter D2, larger than the first diameter D1, over the back portion complementary to the front portion.

The rod 98 is principally of diameter D1 and also comprises two portions 99 of diameter D2, which portions are spaced longitudinally from one another and are in contact with the rear portion of diameter D2 of the cavity of the hollow shaft 36.

A nut 104 screwed onto the front end of the rod 98 holds the ratchet wheel 102 in translation against the shaft 36.

The assembly composed of the ratchet wheel 102 and the rod 98 is integral in translation with the shaft 36, via the screw 104 on the front side and via the portion 99 of diameter D2, larger than the diameter D1, on the back side.

A spring leaf 106, provided with a rectangular opening 108, is fixed to the base 6. When the slide 38 is in the bottom position, the ratchet wheel 102 is in contact with the leaf 106 through the opening 108. The opening 108 in the leaf 106 is at a height such that the ratchet wheel 102 is not in contact with the leaf 106 when the slide 38 is in the top position.

A spring 110 in the form of a wire, visible in FIG. 1, is fixed to the slide 38 and is arranged to permit rotation of the ratchet wheel 102 in one direction only (arrow F).

A resistive sensor 112, in the form of a collar, is fixed to the slide 38. A sliding contact 114, integral with the plate 24, is held in contact with the sensor 112 by way of a spring 116. The purpose of the sensor 112 is to note the number of the filament 22 which is oriented towards the receiving zone 8.

A fork 118 of bent shape comprises a first, substantially vertical portion, which is engaged in an annular groove 120 formed in the back portion of the plate 30, and a substantially horizontal portion connected to an electrical housing 122.

The electrical housing 122 comprises a resistive sensor 123 in contact with the substantially horizontal portion of the fork 118. The purpose of the resistive sensor is to determine the longitudinal spacing of the plate 30 relative to the plate 24, by way of the fork 118. The housing 122 is also connected to the sensor 112 by way of an electric cable 124. The housing 122 comprises a time-lag device capable of immobilizing the rotary shaft 72 for a predetermined period of time, for example 10 seconds.

A device 126 for acquiring information relating to the cutaneous sensibility of the finger 10 of the patient comprises the apparatus 2 and a memory (not shown), which is arranged in the housing 122 and is capable of storing the data received, for each patient, from the sensors 112, 123.

The device 126 comprises means (not shown) for processing the data received from the sensors 112, 123. The device 126 also comprises means for transferring the stored data to external processing means.

Accordingly, during the acquisition of information relating to the cutaneous sensibility of the finger 10 of the patient, by means of the device 126, the patient begins by placing his finger 10 in the receiving zone 8. The finger 10 is positioned laterally by the shape of the cap 4, longitudinally by the stop (not shown), and vertically by the pad 15.

The acquisition of information relating to the cutaneous sensibility of the finger 10 takes place in two stages, a first stage in which the sensation threshold of the finger 10 is determined, and a second stage in which the innervation density of the finger 10 is measured.

During the first stage, the patient must indicate when he perceives the touch of a filament 22 of the first set 20.

A filament 22 of the first set 20 comes into contact with the pulp of the finger 10 through the opening 14 when the slide 38 is in the top position, and is withdrawn when the slide 38 returns to the bottom position. Only the filaments 22 of the first set 20 are involved in this first stage.

At the start of the acquisition, the operator begins by positioning the filament 22 having the smallest diameter in the direction of the receiving zone 8, by manually rotating the plate 24 relative to the shaft 36.

The operator then switches on the apparatus 2. The motor turns the endless screw 76, which drives the shaft 72 in rotation by way of the wheel 74. During normal operation, the shaft 72 rotates through 360° and stops for 10 seconds, by virtue of the time-lag device of the housing 122.

On each turn of the shaft 72, the first cam 46, which is integral with the shaft 72, drives the slide 38 in vertical translation upwards, so that the filament 22 bends in contact with the pulp of the finger 10. The shape of the cam 48 allows the filament 22 to be kept in contact with the finger 10 for about 1.5 seconds. The cam 46 then continues its rotation, driving the slide 38 in translation downwards by the return of the springs 48, so that the filament 22 is not longer in contact with the finger 10.

When the slide 38 is in the bottom position again, the second cam 68 has executed one turn and its tooth comes into contact with a tooth 70 of the plate 30. The second plate 30, as well as the first plate 24 integral in rotation with the second plate 30, then execute a fraction of a turn, with the result that the filament 22 of larger diameter is oriented in the direction of the receiving zone 8. During the following turn of the shaft 72, the filament of larger diameter thus bends in contact with the pulp of the finger 10.

The opening 14 is covered completely by the finger 10, so that the patient cannot know when a filament 22 comes into contact with the pulp of his finger. The patient must indicate to the operator when he has felt the touch of the filament 22. The number of the filament 22, corresponding to a given diameter, is determined by the sensor 112 and then stored in the device 126.

When the patient has felt the touch of a filament 22, the operator has the possibility of manually repositioning the set 20 of filaments 22 in a previous position and beginning the acquisition again, in order to confirm the value found in the first instance.

The operator has the possibility of carrying out a "calibration" of the patient by conducting the same acquisition on the little finger, the sensibility of the pulp of which is controlled by the ulnar nerve, which is not affected by carpal tunnel syndrome.

In the second stage, the operator displaces the second plate 30 in translation towards the first plate 24 until it comes into contact therewith, and orients the pair of filaments 22 of the diameter detected during the first stage towards the receiving zone 8. When the two plates 24, 30 are in contact with one another, the filaments 22 of the selected pair are at a distance of about 1 mm from one another.

Once the plates 24 and 30 are in contact with one another, the operator moves the cam 92 towards its horizontal position, with the result that the internal thread 90 is engaged in the thread 100.

Moving the plate 30 towards the first plate 24 has the effect of disengaging the teeth 70 from the cam 68, so that the second plate 30 is no longer driven in rotation by the cam 68. During the second stage, the objective is to determine the minimum distance between two filaments allowing the patient to detect the touch of both filaments, and the diameter of the filaments is unchanged during this second stage.

As in the first stage, the operator continues the acquisition by switching on the apparatus 2. The shaft 72 executes the same rotary movement as in the first stage, namely a 360° turn, before stopping for 10 seconds. Rotation of the cam 46 causes translation of the slide 38 upwards and downwards alternately.

When the slide 38 passes from the top position to the bottom position, the ratchet wheel 102 is driven in rotation under the effect of contact with the leaf 106.

Because the ratchet wheel 102 is integral in translation with the rod 98, the thread 100 executes a rotation through a fraction of a turn, thus causing translation of the element 84 towards the back. Because the element 84 is integral in longitudinal translation with the second plate 30, the plate 30 is moved backwards slightly away from the first plate 24.

Accordingly, with each cycle of raising and lowering of the slide 38, the spacing between the filaments 22 of the selected pair increases.

The opening 108 in the leaf 106 is of such a size that the ratchet wheel 102 is driven in rotation only when the filaments 22 are away from the opening 14. Accordingly, the two filaments 22 are moved away from one another when they are no longer in contact with the pulp of the finger 10.

The patient must indicate to the operator when he perceives the touch of two distinct points. The spacing between the two filaments 22 is then determined with the aid of the sensor 123 by way of the fork 118, and stored in the device 126.

During the second stage, the operator has the possibility of disengaging the internal thread 90 from the thread 100 by acting on the cam 92. The operator then has the possibility of bringing the plate 30 up to the plate 24 again manually and thus repeating the acquisition in reverse, in order to confirm the spacing previously determined.

The compilation of the two data resulting from the first stage and the second stage characterizes the state of the patient's median nerve. They are stored in the device 126 in order to be transferred to external processing means and also for the purpose of comparison with other acquisitions carried out on the same patient.

The data from the sensors 112 and 123 are also available to the operator during the acquisition by way, for example, of a standard ohmmeter equipped with a liquid crystal screen.

If the acquisition of the information relating to the cutaneous sensibility of the finger 10 shows a loss of sensibility indicating damage to the median nerve, hospital confirmation is required with the aid of an electromyogram or EMG, which allows the clinical situation of the patient to be identified.

In a variant, the filaments 22 are disposed on the first plate 24 and on the second plate 30 according to a random progression of their diameters.

In a variant, the data from the sensors 112 and 123 are readable, during the acquisition, from a display present on a lateral face of the cap 4.

Of course, other embodiments can be envisaged.

The invention claimed is:

1. An apparatus (2) for the early diagnosis of carpal tunnel syndrome, of the type comprising:
    receiving means which define a receiving zone (8) for receiving a patient's finger,
    means for measuring the cutaneous sensibility of a finger (10) disposed in said receiving means, comprising a device for determining a sensation threshold (16) of the finger pulp and a device for measuring the innervation density (18) of the finger pulp, each device comprising protruding portions (22) adapted to be brought into contact with the finger (10),
characterized in that the protruding portions (22) of the device for measuring the innervation density (18) are identical with those of the device for determining the sensation threshold (16), and the device for determining the sensation threshold (16) comprises a first set (20) of at least two filaments (22) of different diameters, means for selecting a filament of said first set (20), and means for displacing the selected filament (22) towards the receiving zone (8), parallel to the direction of said selected filament (22).

2. The apparatus (2) according to claim 1, characterized in that the device for measuring the innervation density (18) of the finger (10) comprises a pair of identical sets (20, 28) of filaments (22), each set (20, 28) comprising at least two filaments (22) of different diameters, means for selecting a pair of filaments (22) of identical diameters and positioning them parallel with one another, each filament (22) of said pair belonging to one of said sets (20, 28) of filaments (22), means for adjusting the distance between the filaments (22) of the selected pair, and means for displacing the selected pair of filaments (22) towards the receiving zone (8) parallel to the direction of said filaments (22) of the selected pair.

3. The apparatus (2) according to claim 2, characterized in that it comprises a shaft (36) and at least one support means (24, 30), which is mounted freely in rotation about the shaft (36) and is displaceable in translation in a direction perpendicular to the shaft (36), each set (20, 28) of filaments (22) being disposed on a support means (24, 30), said filaments (22) being oriented in radial direction relative to the shaft (36).

4. The apparatus (2) according to claim 3, characterized in that the selection and positioning means, respectively, comprise a second cam (68) which is arranged to cause each support means (24, 30) to rotate about the shaft (36).

5. The apparatus (2) according to claim 1, characterized in that the set (20) of the filaments (22) of the device for determining the sensation threshold (16) is one of the two sets (20, 28) of filaments (22) of the device for measuring the innervation density (18).

6. The apparatus (2) according to claim 1, characterized in that it comprises a shaft (36) and at least one support means (24, 30), which is mounted freely in rotation about the shaft (36) and is displaceable in translation in a direction perpendicular to the shaft (36), each set (20, 28) of filaments (22) being disposed on a support means (24, 30), said filaments (22) being oriented in radial directions relative to the shaft (36).

7. The apparatus (2) according to claim 6, characterized in that the displacement means comprise a slid (38) for supporting the shaft (36), means (44) for supporting said slide (38) in translation, and a first cam (46) which is arranged to displace the slide (38) along the support means (44) in an alternating movement in the direction towards, and then away from, the receiving zone (8).

8. The apparatus (2) according to claim 6, respectively, characterized in that the selection means, or the selection and positioning means, respectively, comprise a second cam (68) which is arranged to cause each support means (24, 30) to rotate about the shaft (36).

9. The apparatus (2) according to claim 8, characterized in that it comprises means for disengaging the selection means, respectively for selecting and positioning means, so as to allow an operator conducting a test for measuring the sensibility of the patient's finger to orient a chosen filament (22), respectively a chosen pair of filaments (22), towards the receiving zone (8).

10. The apparatus (2) according to claim 8, characterized in that it comprises an electrical device for driving second cam (68) rotation.

11. The apparatus (2) according to claim 6, characterized in that the adjustment means comprise a ratchet wheel (102) mounted for rotation on the shaft (36), said wheel (102) being in contact with a spring leaf (106), a first support means (24) being integral in translation with the ratchet wheel (102) and a second support means (309 being free in translation relative to said wheel (102) in its axial direction, an internally threaded element (84) mounted on the second support means (30), a rod (98) which is integral with the ratchet wheel (102) at one end, is threaded at the other end, and is mounted inside the shaft (36), and means for translation of the internally threaded element (84) towards a position in which it is engaged on the threaded rod (98), so that, when the internally threaded element (84) is in the engaged position on the threaded rod (98), each translation of the slide (38) away from the receiving zone (8) causes rotation of the ratchet wheel (102), causing translation of the second support means (30) relative to the first support means (24) in the axial direction of the shaft (36), said translation altering the distance between the filaments (22) of the selected pair.

12. The apparatus (2) according to claim 7, characterized in that it comprises an electrical device for driving first cam (46) rotation.

13. The apparatus (2) according to claim 1, respectively, characterized in that it comprises means (112) for determining the selected filament (22), respectively the selected pair of filaments (22).

14. The apparatus (2) according to claim 1, characterized in that it comprises means (123) for determining the distance between the filaments (22) of the selected pair.

15. A device (126) for acquiring information relating to the cutaneous sensibility of a finger of a patient, of the type characterized in that it comprises an apparatus (2) for the early diagnosis of carpal tunnel syndrome according to claim 1, and means for storing the output signal of the determination means (112, 123).

16. A method of acquiring information relating to the cutaneous sensibility of a finger of a patient by means of a device (126) for acquiring said information, said device (126) comprising a pair of identical sets (20, 28) of filaments (22), and said method comprising steps in which:
- a sensation threshold of the finger pulp is measured and stored by determining the minimum diameter of the filament (22) of a first set (20) of filaments (22) for which the patient perceives the touch of said filament (22), and
- without the patient's finger moving in relation to the preceding step, an innervation density of the finger pulp is measured and stored by determining the minimum spacing between two filaments (22), which are identical and have the diameter determined in the preceding step, for which the patient distinctly perceives the touch of both filaments (22).

17. The method according to claim 16, comprising, for measuring and storing the sensation threshold of the finger pulp, steps in which:
- filaments (22) of the first set (20) are brought into contact, in succession, with the finger pulp, according to an increasing or random progression of their diameters,
- the number of the filament for which the patient perceives the touch of said filament (22) is determined, and
- the number of said filament is stored.

18. The method according to claim 16, comprising, for measuring and storing the innervation density of the finger pulp, steps in which:
- a pair of filaments (22) having the diameter determined in the step of measuring the sensation threshold of the finger pulp is brought into contact with the finger pulp, with an initial spacing of about 1 mm,
- the two filaments (22) of said pair of filaments (22) are gradually moved apart,
- the minimum distance between said two filaments (22) for which the patient distinctly perceives the tough of both filaments (22) is determined, and
- said minimum distance is stored.

\* \* \* \* \*